US008652771B2

(12) United States Patent
Peti-Peterdi

(10) Patent No.: US 8,652,771 B2
(45) Date of Patent: Feb. 18, 2014

(54) MEASUREMENT OF SUCCINATE IN URINE SAMPLES AS A BIOMARKER OF KIDNEY DAMAGE IN DIABETIC SUBJECTS

(75) Inventor: Janos Peti-Peterdi, Pasadena, CA (US)

(73) Assignee: University of Souther California, Los Angeles, CA (US)

( * ) Notice: Subject to any disclaimer, the term of this patent is extended or adjusted under 35 U.S.C. 154(b) by 96 days.

(21) Appl. No.: 12/473,135

(22) Filed: May 27, 2009

(65) Prior Publication Data

US 2009/0298188 A1 Dec. 3, 2009

Related U.S. Application Data

(60) Provisional application No. 61/056,782, filed on May 28, 2008.

(51) Int. Cl.
C12Q 1/25 (2006.01)
(52) U.S. Cl.
USPC .................. 435/4; 436/129; 436/175
(58) Field of Classification Search
None
See application file for complete search history.

(56) References Cited

PUBLICATIONS

Nicholson, J. K. et al. "Protein NMR Spectra of Urine as Indicators of Renal Damage," Molecular Pharmacology 1985, 27, 644-651.*
Miwa, H. et al. "High-Performance Liquid Chromatographic Analyses of Hydroxymonocarboxylic Acids and Dicarboxylic Acids in Urine as their 2-Nitrophenylhydrazides," Analytical Biochemistry 1990, 185, 17-23.*
Le Moyec, L. et al. "Protein Nuclear Magnetic Resonance Spectroscopy of Urine and Plasma in Renal Transplant Follow-Up," Nephron 1993, 65, 433-439.*
Nava, M. et al. "Melatonin attenuates acute renal failure and oxidative stress induced by mercuric chloride in rats," Am J Physiol Renal Physiol 279: F910-F918, 2000.*
Ildikó Toma, et al.: "*Imaging Renin Content and Release in the Living Kidney*"; Nephron Physiology, (2006);103: pp. 71-74.
Timo Wittenberger, et al. "*An Expressed Sequence Tag (EST) Data Mining Strategy Succeeding in the Discovery of New G-Protein Coupled Receptors*"; J. Mol. Biol. (2001); 307, pp. 799-813.
Weihal He., et al. "Citric acid cycle intermediates as ligands for orphan G-protein-coupled receptors"; Nature. 2004; vol. 429: pp. 188-193.
L. Baumbach, et al.; "*Studies on Renin Release From Isolated Superfused Glomeruli: Effects of Temperature, Urea, Ouabain and Ethacrynic Acid*"; J. Physiol. (1976); vol. 258, pp. 243-256.
Nalini Sadagopan, et al.: "*Circulating Succinate is Elevated in Rodent Models of Hypertension and Metabolic Disease*"; American Journal of Hypertension, Ltd. (2007); vol. 20: pp. 1209-1215.

* cited by examiner

*Primary Examiner* — Yelena G Gakh
*Assistant Examiner* — Michelle Adams
(74) *Attorney, Agent, or Firm* — DLA Piper LLP (US)

(57) ABSTRACT

The present invention relates in general to the discovery of urinary succinate as a novel biomarker of kidney disease. More specifically, the invention provides for the measurement of succinate in urine samples that has great potential for the easy and early diagnosis of kidney damage and would allow early prediction of kidney disease and therapeutic intervention.

7 Claims, 7 Drawing Sheets

MEASUREMENT OF SUCCINATE IN URINE SAMPLES AS A BIOMARKER OF KIDNEY DAMAGE IN DIABETIC SUBJECTS

The present application claims the benefit of the filing date of U.S. Provisional Application No. 61/056,782 filed May 28, 2008, the disclosure of which is incorporated herein by reference in its entirety.

FUNDING

This invention was made with government support under Contract No. DK74754 awarded by National Institutes of Health. The government has certain rights in the invention.

FIELD OF THE INVENTION

The present invention relates in general to kidney disease. More specifically the invention provides methods of measuring urinary succinate as a novel biomarker and early predictor of kidney disease.

BACKGROUND OF THE INVENTION

More than 500 million people worldwide (10% of the adult population) have some form of kidney damage, and every year millions die prematurely of cardiovascular diseases linked to chronic kidney disease. Diabetes mellitus (DM) is the most common and rapidly growing cause of end-stage renal disease in developed countries. The incidence of diabetes mellitus and obesity are rapidly rising to epidemic levels in the United States and worldwide. Hyperglycemia, the metabolic hallmark of the pathology is a significant causative factor for the complications of diabetes mellitus, which results in significant morbidity and mortality for millions of Americans.

Renin-angiotensin system (RAS) activation in diabetes mellitus and the metabolic syndrome is a core abnormality that leads to many complications of the disease, including hypertension, proteinuria, and renal tissue injury (1, 2). It has been difficult to isolate acute and direct actions of hyperglycemia on glomerular structures from the systemic factors and complex intrarenal feedback mechanisms (3) that can indirectly activate the RAS. Therefore, the primary cause and exact mechanism of RAS activation in early diabetes is still elusive.

The G protein-coupled receptor, GPR91, which functions as a detector of cell metabolism (4, 5), may provide a new, direct link between hyperglycemia and RAS activation. Its ligand, the TCA cycle intermediate succinate (4), which is normally present in the mitochondria, can be released extracellularly if the local tissue energy supply and demand is out of balance (5). Succinate accumulation caused by restricted organ blood supply (local ischemia), GPR91 activation, and subsequent renin release has been recently implicated in the development of renovascular hypertension (4). GPR91 is present in many organs, including the kidney, liver, spleen, breast, and blood vessels, but it is expressed most abundantly in the kidney (4, 6). In the renal cortex, GPR91 was detected in various nephron segments and in the juxtaglomerular apparatus (JGA) (4), although the specific cellular localization has not been determined.

The JGA represents the major structural component of the RAS and is one of the most important regulatory sites of systemic blood pressure (7-9). Renin-producing juxtaglomerular (JG) cells, located in the wall of the terminal afferent arteriole, are key components of the JGA and receive numerous chemical signals from adjacent vascular endothelial, smooth muscle, and tubular epithelial cells that precisely control the rate of renin release (8). Classic chemical mediators that stimulate renin release include prostaglandins (PGE2 and PGI2) and NO (8, 9). Release of renin from JG cells is considered the rate-limiting step of RAS activation, and it ultimately leads to the generation of Ang II, the main RAS product and the primary effector of pathology in diabetes (1). In addition, the renin precursor prorenin, which is also produced and released by JG cells, has been directly implicated in diabetic nephropathy (10).

Succinate has been shown to cause the release of the hypertensive hormone renin from the kidney (11). Consistent with the key role of succinate as a signaling molecule for GPR91 activation, and its involvement in the pathogenesis of hypertension and metabolic diseases, the accumulation of succinate in plasma samples was recently reported (21). However, this was observed only in rodent models and not in humans (21). At the same time, our laboratory demonstrated local accumulation of succinate in the diabetic kidney tissue to levels that are consistent with GPR91 activation (13). We measured succinate in non-diabetic and diabetic kidney tissue and urine samples. In freshly harvested urine and whole kidney tissue samples of non-diabetic mice the succinate concentration was 26±7 and 10±0.2 µM, respectively. In contrast, 1-2 orders of magnitude higher levels were detected in samples from diabetic animals (168±45 µM in urine, 616±62 µM in tissue). This new finding indicates that urinary succinate rather than plasma succinate should be measured as a sign of kidney tissue damage. Our data are consistent with the local accumulation of succinate in the damaged kidney tissue which is reflected in urinary succinate levels (13). In addition to rodent tissue and urine, we now have supporting data using human urine samples that urinary succinate is a potential biomarker and an early predictor of kidney disease in humans. In a recent, unpublished clinical study consisting of 90 patients we found that succinate content of spot human urine samples (using the succinate/creatinin ratio which is independent of urinary concentration/dilution) was increased 4-fold in diabetic patients with chronic kidney disease (FIG. 9). This further suggests the importance of the succinate-GPR91 signaling pathway in kidney disease as well as the utility of this novel biomarker, similar to the mechanism described in rodent kidneys. Succinate is not only the direct cause of pathology, but urinary succinate can be used as an ideal biomarker of kidney tissue damage. and an early predictor of pathology. Because of the newly discovered GPR91 receptor and its role in RAS activation (4), we believe that it is a (patho)physiologically significant mediator by which high levels of glucose supply and metabolism at the onset of diabetes directly cause renin release through succinate and GPR91 signaling in the JGA.

SUMMARY OF THE INVENTION

In one embodiment, the invention relates to non-invasive methods for determining kidney damage in a subject. The method comprises comparing the expression levels of succinate in a sample to that of a control. If the levels of expression of succinate in the sample are greater than the levels of expression of succinate in the control, then kidney damage has been determined.

In a related embodiment, the invention relates to non-invasive methods for determining high glucose levels in a subject. The method comprises comparing the expression levels of succinate in a sample to that of a control. If the levels of expression of succinate in the sample are greater than the levels of expression of succinate in the control, then high glucose levels have been determined.

In accordance with another embodiment, the invention relates to non-invasive methods for determining kidney damage in a subject. The method comprises comparing the succinate/creatinine ratio expression levels of a sample to that of a control. If the succinate/creatinine ratio expression levels in the sample are greater than the levels in the control, then kidney damage has been determined.

In a closely related embodiment, the invention relates to methods for predicting the early onset of kidney disease in a subject. The method comprises comparing the expression levels of succinate in a sample to that of a control. If the levels of expression of succinate in the sample are greater than the levels of expression of succinate in the control, then early onset of kidney disease has been predicted.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
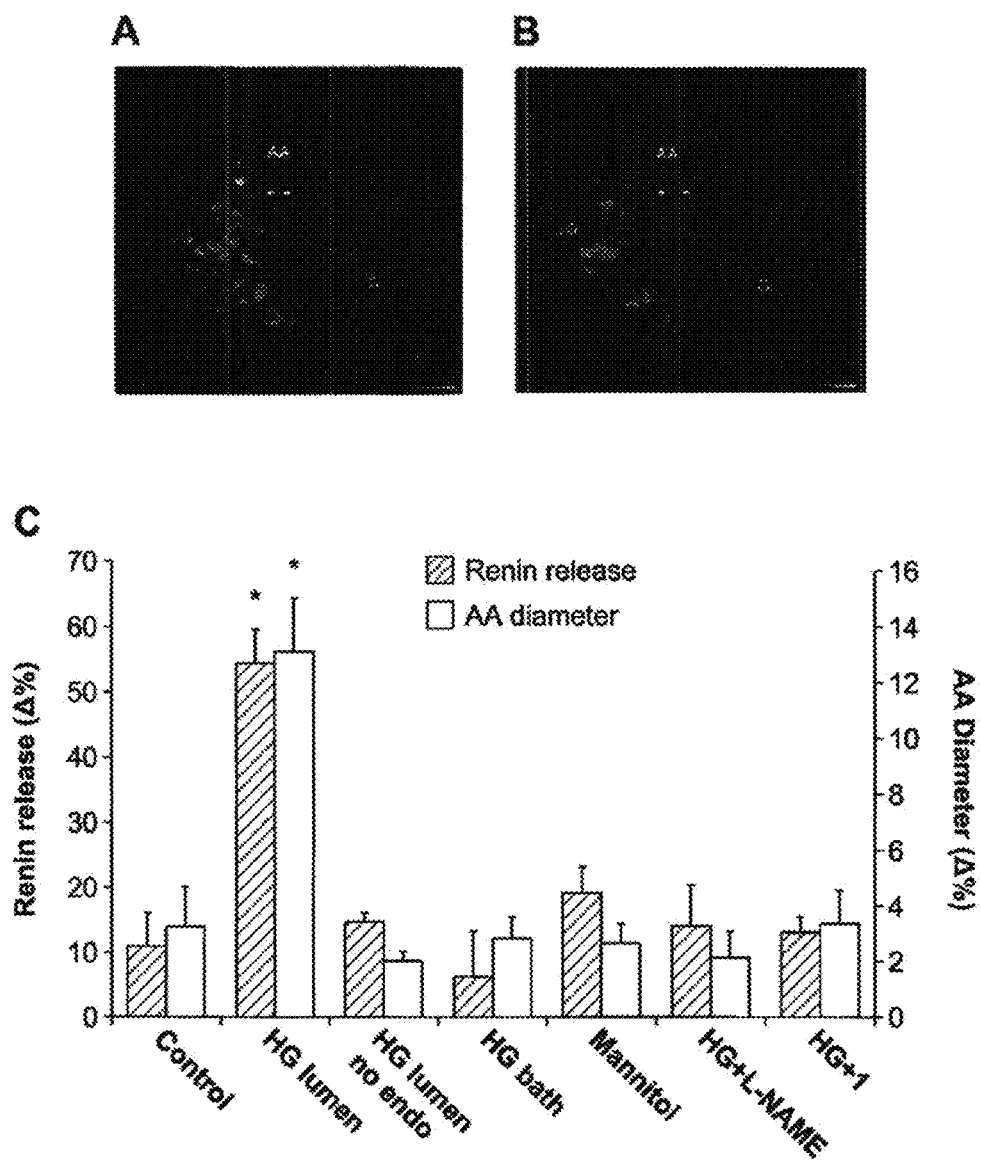
FIG. 1: Direct and acute effects of high glucose level on the JGA. (A and B) Real-time confocal fluorescence imaging of renin content (quinacrine, light gray) and vascular diameter (cell membranes are labeled with R-18, dark gray) in the in vitro microperfused terminal afferent arteriole (AA) with attached glomerulus (G) freshly isolated from rabbit kidney. In response to increasing glucose concentration of the afferent arteriole perfusate from 5.5 mM (control, A) to 25.5 mM (high glucose level, B), a significant number of renin granules in JG cells (JG) released their fluorescent content and the afferent arteriole internal diameter (arrows) increased. Scale bar: 20 µm. (C) Normalized reductions in quinacrine fluorescence (as an index of renin release) and increases in afferent arteriole diameter within 30 minutes of high glucose level (HG) application. Blockade of NO synthases (L-NAME; 1 mM) and cyclooxygenases ([I]indomethacin; 50 µM) inhibited the effects of high glucose level, indicating involvement of NO and prostaglandins, respectively. Removing the endothelium (endo) or bath glucose had no effect, and equimolar mannitol caused only minor renin release. *$P<0.01$; n=6 each.

The existence of high levels of succinate in the urine may be indicative of kidney tissue damage of several origin including reduced blood supply, hypertension, metabolic diseases such as diabetes mellitus, metabolic syndrome, etc. The accurate and reliable determination of succinate concentrations in urine would therefore provide an easily performed, non-invasive procedure for the detection of kidney damage. Such a procedure should be used in routine medical exams and check-ups, and not only in high risk groups such as diabetic and hypertensive patients. This procedure would obviate the need to draw blood for analysis of kidney function (currently used), or would replace other high-cost diagnostic tests such as ultrasound, CT, MRI, or the use of radioisotopes. Development of a succinate strip (similar to glucose strips) to be used in fresh urine samples would provide a painless and convenient approach to monitor kidney function of an individual.

Currently, only one commercial product, an enzyme-based succinate assay from Boehringer Mannheim Corporation, is available for succinate determination. This test has been developed however, for the determination of succinate from food samples and it is not sensitive enough to low succinate concentrations or in general, not useful for urine samples. Consequently, the potential market for a new diagnostic tool is enormous.

Succinate accumulation in urine samples of diabetic animals was measured as a proof of concept using the Boehringer assay (13).

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Materials and Methods

Animals.

All experiments were performed with the use of protocols approved by the Institutional Animal Care and Use Committee at the University of Southern California (USC). Female New Zealand rabbits (about 500 g) were purchased from Irish farms. Breeding pairs of GPR91+/− mice (C57BL/6 background) were provided by Amgen and were bred at USC. Animals were housed in a temperature-controlled room under a 12-hour light-dark cycle with water and standard chow available ad libitum. In some mice, the STZ model of type 1 diabetes was used as described before (15, 33). Briefly, diabetes was induced by daily i.p. STZ (50 mg/kg) injections for 4 days. Blood was collected from tail vein, and blood glucose levels were measured with test strips (Freestyle Blood Glucose Monitoring System; Abbott Laboratories) to confirm the successful induction of diabetes (blood glucose levels greater than 400 mg/dl). Animals were studied within 4 weeks after STZ injection, during the early phase of diabetes.

Genotyping of Mice.

Mice were characterized by PCR using genomic DNA extracted from tail biopsies. DNA was digested with the REDExtract-N-Amp Tissue PCR Kit (Sigma-Aldrich). Routine genotyping by PCR was performed using the following primers:

```
Neo3A    (5'-GCAGCGCATCGCCTTCTATC-3'),
GPR91-/-reverse  (5'-GCTGCCTTCTGATTCATGTGG-3'),
and GPR91-/-forward  (5'-GTCGTCTGGGCCTTAGTGACC-3').
```

In Vitro Microperfusion.

A superficial afferent arteriole with its glomerulus was microdissected from freshly harvested kidney slices. The afferent arteriole was cannulated and perfused using a method similar to those described previously (37). Briefly, dissection media were prepared from DMEM mixture F-12 (Sigma-Aldrich). Fetal bovine serum (Hyclone) was added at a final concentration of 3%. Vessel perfusion and bath fluid was a modified Krebs-Ringer-HCO3 buffer containing 115 mM NaCl, 25 mM NaHCO3, 0.96 mM NaH2PO4, 0.24 mM Na2HPO4, 5 mM KCl, 1.2 mM MgSO4, 2 mM CaCl2, 5.5 mM d-glucose and 100 μM l-arginine. The solutions were aerated with 95% O2 and 5% CO2 for 45 minutes, and their pH was adjusted to 7.4. Each preparation was transferred to a thermoregulated Lucite chamber mounted on the Leica inverted microscope. The preparation was kept in the dissection solution, and also, temperature was kept at 4° C. until cannulation of the arteriole was completed and then was gradually raised to 37° C. for the remainder of the experiment. In some experiments, the endothelium was mechanically removed from the vessel wall with the help of the perfusion pipette and by perfusing the control solution under the endothelium (between the endothelium and smooth muscle). This maneuver resulted in the detachment of the endothelial layer from the smooth muscle-JG cells. The bath was continuously aerated with 95% O2 and 5% CO2. The acidotropic fluorophore quinacrine (Sigma-Aldrich), which is an intravital fluorescent dye selective for dense-core secretory granules, was used for labeling the renin granules (12, 13, 15). The membrane staining octadecyl rhodamine B chloride R18 and the nuclear stain Hoechst 33342 were used to visualize the glomerulus with its attached afferent arteriole. For ratiometric Ca2+ imaging, the fluo-4/fura red pair was used and calibrated as described before (37). DAF-FM was used to monitor changes in NO production as described (38). All fluorophores were from Invitrogen.

Multiphoton Fluorescence Microscopy.

Preparations were visualized using a 2-photon laser scanning fluorescence microscope (TCS SP2 AOBS MP confocal microscope system; Leica-Microsystems). A Leica DM IRE2 inverted microscope was powered by a wideband, fully automated, infrared (710-920 nm), combined photo-diode pump laser and mode-locked titanium:sapphire laser (Mai-Tai; Spectra-Physics) for multiphoton excitation and/or by red (HeNe 633 nm/10 mW), orange (HeNe 594 nm/2 mW), green (HeNe 543 nm/1.2 mW) and blue (Ar 458 nm/5 mW; 476 nm/5 mW; 488 nm/20 mW; 514 nm/20 mW) lasers for conventional, 1-photon-excitation confocal microscopy. Images were collected in time-series (xyt) and analyzed with Leica LCS imaging software.

Cell Culture.

TsAS58 immorto mice GENCs (a generous gift from N. Akis, Halic University, Istanbul, Turkey) have been characterized before (14) and were grown to confluence in 10% DMEM, 25 mM HEPES, 9 mM NaHCO3, 7.5% new born calf serum (Gibco), and 1% penicillin/streptomycin in a humidified (95% O2 and 5% CO2) incubator at 37° C. Afferent arteriolar VSMCs and JG renin-producing cells were freshly isolated from C57BL/6 mouse kidneys using available techniques (39-41).

Succinate Assay.

Kidney tissue and urine succinate concentration was determined using a cuvette-based enzymatic assay according to manufacturer's instructions (Boehringer Mannheim/R-Biopharm AG). Briefly, the enzymatic reaction measures the conversion of succinate by succinyl-CoA synthetase, pyruvate kinase, and l-lactate dehydrogenase and the stoichiometric amount of NADH oxidized in the reaction. By measuring the absorbance at 340 nm (UV detection), the amount of succinate can be calculated from the amount of NADH oxidized. Whole kidney tissue and urine samples were freshly harvested from nondiabetic and diabetic GPR91+/+ mice. The kidneys of anesthetized, live animals were first flushed with ice-cold PBS injected through the heart and then removed and immediately homogenized on ice in a buffer containing 20 mM Tris-HCL, 1 mM EGTA, pH 7.0, and a protease inhibitor cocktail (BD Biosciences), similar to that described below for western blotting. Urine samples were removed from the bladder and diluted 1:20 with water. Prior to measurements, protein content of kidney homogenates and urine samples was eliminated by using 1 M perchloric acid, which was then neutralized by 2 M KOH. The precipitant was filtered and the pH of the clear solutions was adjusted to 8.5. A reaction solution was combined per kit instructions and incubated with the sample at 37° C. for 5 minutes before reading the absorbance of the sample. After 20 minutes of incubation at 37° C., samples were again measured for completion of the assay. The absorbance value was compared against a blank and the concentration was determined.

PGE2 Biosensor Technique.

Generation of HEK293-EP1 cells as PGE2 biosensors and their use has been described before (42).

RT-PCR.

Total RNA was purified from confluent tsA58 mouse-derived GENC line, afferent arteriolar VSMCs, JG cells, and whole kidney tissue of GPR91+/+ and GPR91−/− mice using a Total RNA Mini kit (Bio-Rad). RNA was quantified using spectrophotometry and reverse-transcribed to single-stranded cDNA using avian reverse-transcritpase and random hexamers according to the manufacturer's instructions (Thermoscript RT-PCR System; Invitrogen). cDNA (2 µl) was amplified using a master mix containing Taq polymerase (Invitrogen) and the following primers: GPR91 sense, 5'-TGTGAGAATTGGTTGGCAACAG-3'; GPR91 antisense, 5'-TCGGTCCATGCTAATGACAGTG-3', each at a final concentration of 100 µM. The PCR reaction was carried out for 30 cycles of the following: 94° C. for 30 seconds, 55.4° C. for 30 seconds, and 72° C. for 30 seconds. The PCR product was analyzed on a 2% agarose gel to identify GPR91 fragments of approximately 330 bp.

siRNA Interference of GPR91 in GENCs.

On the first day of the study, GENCs were trypsinized, and cells were resuspended at a concentration of 100,000 cells/ml in antibiotic-free complete DMEM medium. Then, 100 µl of cell suspension was added to each well of a 96-well plate and incubated overnight at 37° C. with 5% CO2. The next day, GENCs were transfected employing the protocols validated for the DharmaFECT 1 Transfection Reagent and ON-TARGETplus SMARTpool of 4 GPR91 siRNAs (Dharmacon). Media were removed from each well of the 96-well plate, and 100 µl of transfection medium was then added to each well. Cells were incubated at 37° C. in 5% CO2 for 48 hours, transferred to larger plates, and then cultured in complete GENC medium for studies. RNA was extracted from cells and amplified to validate inhibition of GPR91 synthesis. Functional confirmation of GPR91 knockdown was provided by fluorometric studies on cells. Cells retained adequate GPR91 silencing for at least 3 passages.

Immunohistochemistry.

GPR91 polyclonal antibody (Millipore) and rat endothelial marker RECA (mouse anti rat RECA-1; AbD Serotec) antibody were used on mouse, rat, and rabbit kidney sections as described before (12, 42). GENCs, VSMCs, and JG renin granular cells on glass coverslips were fixed in 4% formalin for 10 minutes and permeabilized with 0.1% Triton-X in PBS for 5 minutes. Sections were blocked with goat serum (1:20) and incubated overnight with an affinity-purified antibody against the endothelial cell marker CD31 (1:50; Abcam), α-smooth muscle actin (1:400; Sigma-Aldrich), or renin (1:100; a generous gift from T. Inagami, Vanderbilt University, Nashville, Tenn., USA). This was followed by 1-hour incubation with a AF594- or AF488-conjugated secondary antibody (1:200; Invitrogen). The GPR91 signal was enhanced with AF594-labeled tyramide signal amplification (TSA) according to the manufacturer's instructions (Invitrogen). Sections were mounted with VECTASHIELD media, containing DAPI for nuclear staining (Vector Laboratories).

Western Blot Analysis.

Manually dissected slices of kidney cortex were homogenized in a buffer containing 20 mM Tris-HCl, 1 mM EGTA, pH 7.0, and a protease inhibitor cocktail (BD Biosciences). Forty micrograms of protein were separated on a 4%-20% SDS-PAGE and transferred onto PVDF membrane. The blots were blocked for a minimum of 1 hour with Odyssey Blocking Buffer (LI-COR Biosciences) at room temperature. This was followed by an incubation of the primary antibody (1:5,000 renin; Fitzgerald) overnight at 4° C., along with β-actin (1:5,000; Abcam) in 2.5 ml 1×PBS (OmniPUR; VWR), 2.5 ml Odyssey Blocking Buffer (LI-COR Biosciences), and 5.0 μl Tween 20 solution (Sigma-Aldrich). After washing with PBS-T, 1×PBS plus 1:1,000 Tween 20, blots were incubated in 2.5 ml PBS, 2.5 ml Blocking Buffer, 5.0 μl Tween 20, and 5.0 μl 10% SDS, with a goat anti-mouse (1:15,000; LI-COR Biosciences) and a goat anti-rabbit secondary antibody (1:15,000; LI-COR Biosciences), and then were visualized with Odyssey Infrared Imaging System, Western Blot Analysis (LI-COR Biosciences).

Trypsinization Protocol.

Prorenin was evaluated as the difference in renin activity before (active renin) and after trypsinization (total renin). Kidney homogenates were collected from nondiabetic and diabetic mice as described above. Plasma samples were derived from whole blood collected by cardiac puncture and centrifuged for 10 minutes at approximately 3,000 g and −4° C. Trypsinization activates prorenin to renin (43). Samples were trypsinized (50 g/l) for 60 minutes on ice and reaction stopped with Soybean Trypsin Inhibitor (100 g/l) for 10 minutes on ice. Renin activity was evaluated by cuvette-based fluorometry (Quantamaster-8; Photon Technology Inc.) using a FRET-based renin substrate assay as described previously (16). Substrate was present in excess, so the initial reaction rate (within 50 seconds of adding 40 μg sample) estimated renin activity, using Felix software (Photon Technology Inc.). Trypsin in the presence of trypsin inhibitor did not interact with renin substrate.

Spectrofluorometry.

$[Ca^{2+}]i$ of GENCs was measured with dual excitation wavelength fluorometry (Quantamaster-8; Photon Technology Inc.) in a cuvette-based system using the fluorescent probe fura-2. Fura-2 fluorescence was measured at an emission wavelength of 510 nm in response to excitation wavelengths of 340 and 380 nm. Emitted photons were detected by a photomultiplier. Autofluorescence-corrected ratios (340:380) were calculated at a rate of 5 points/sec using Photon Technology Inc. software. GENCs were loaded with fura-2 AM (10 μM) for 30 minutes. The 340:380 ratios were converted into $Ca^{2+}$ values as described before (44).

In Vivo Experiments.

Male GPR91+/+ and GPR91−/− mice (8-10 weeks of age) were anesthetized using ketamine (50 mg/kg) and inactin (130 mg/kg) and instrumented for multiphoton in vivo imaging of the intact kidney as described before (15, 45). Briefly, the femoral artery was cannulated in order to monitor systemic blood pressure, using an analog single-channel transducer signal conditioner model BP-1 (World Precision Instruments). The left femoral vein was cannulated for infusion of dye, such as quinacrine (Sigma-Aldrich), and rhodamine-conjugated 70,000 MW dextran (Invitrogen). The kidney was exteriorized via a small dorsal incision. The animal was placed on the stage of the Leica IRE2 inverted microscope with the exposed kidney placed in a coverslip-bottomed, heated chamber and the kidney was bathed in normal saline.

Statistics.

Data are expressed as mean±SEM. Statistical significance was tested using 1-way ANOVA. Significance was accepted at $P<0.05$.

Results

High Glucose Level Directly Triggers Renin Release In Vitro.

Direct and acute effects of high glucose levels on the JGA were studied free of systemic influences, using a well established in vitro approach (12, 13) that combines a JGA microperfusion model with fluorescence confocal imaging. Increasing glucose concentration of the afferent arteriole perfusate triggered renin release and vasodilatation of the afferent arteriole within a few minutes (FIG. 1). Within 30 minutes of high levels of glucose application, JGA granular content was reduced by 54±5Δ% (where Δ% means the change in quinacrine fluorescence intensity [F0-F] normalized to the baseline [F0]) compared with control basal release (11±5Δ%), and the afferent arteriole dilated significantly. These effects of high glucose level were endothelium dependent, since removing the endothelium of the afferent arteriole (14±1Δ%) or bath application of high glucose level (6±7Δ%) had no effect on renin release. The use of mannitol to control for the effect of osmolality resulted in only minor renin release (19±4Δ%). The actions of high glucose level most likely involved NO and prostaglandins, since both NO synthase and cyclooxygenase inhibition abolished the effects of application of high levels of glucose (14±6Δ% and 13±2Δ% renin release, respectively). Similar effects were observed on the vascular tone.

Involvement of the TCA Cycle Intermediate Succinate.

Figure 2:
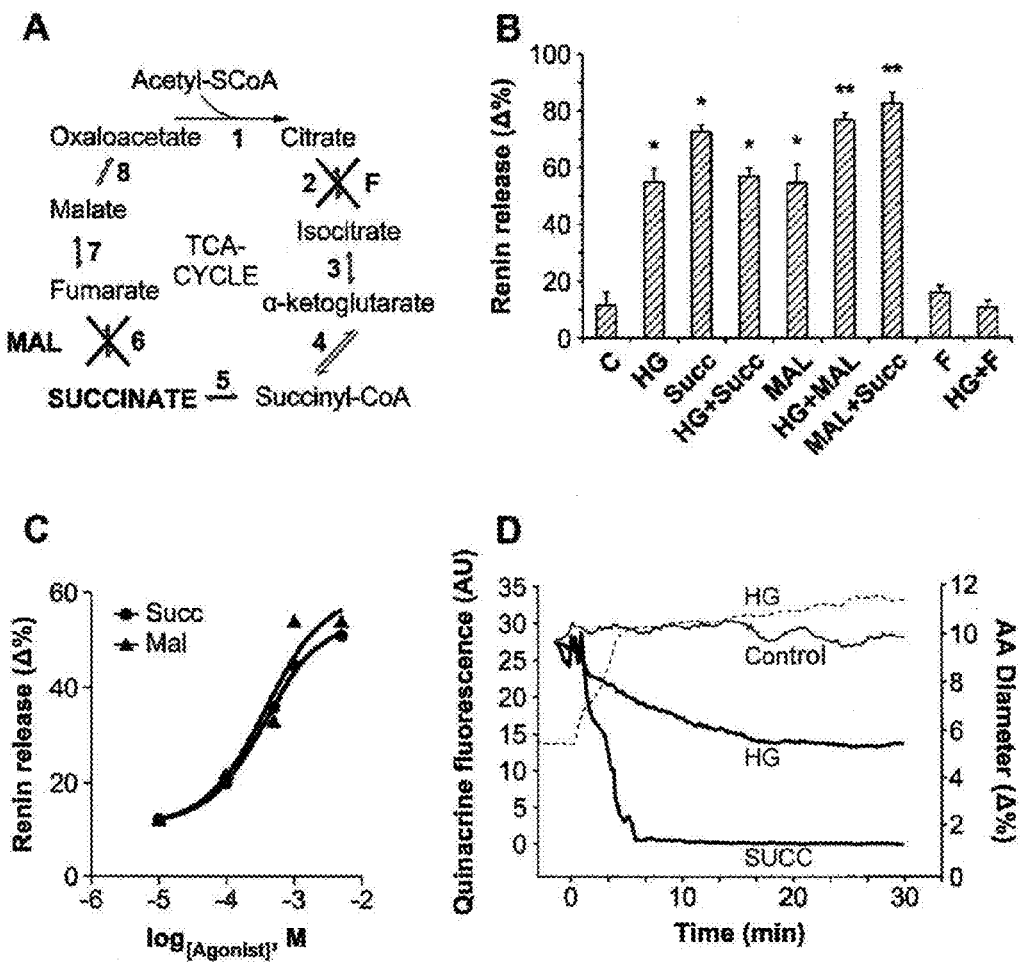
FIG. 2: Effects of TCA cycle intermediates and inhibitors on renin release. (A) Overview of the TCA cycle and sites of inhibition with fluorocitrate (F: 100 µM: blocks aconitase in step 2) and malonate (MAL; 1 mM; blocks succinate dehydrogenase in step 6). (B) Effects of TCA cycle inhibitors on renin release in presence of normal (5.5 mM when not indicated) or high glucose (25.5 mM), or succinate (SUCC, 5 mM) levels. C, control. *$P<0.001$, control vs. high glucose, high glucose plus succinate, succinate, and malonate. **$p<0.001$ malonate alone vs. malonate plus high glucose, and malonate plus succinate. n=6 each. (C) Dose-dependent effects of succinate and malonate on in vitro renin release. n=6 measurements for each dose. (D) Representative recordings of changes in quinacrine fluorescence intensity (renin release) in control and in response to high glucose and succinate levels (black lines), and the time course of the high glucose level-induced afferent arteriole vasodilatation (dotted line).

Since it was established earlier that succinate causes renin release (11), we tested whether the mechanism of the high-level-of-glucose effect involves the TCA cycle. The effects of various TCA cycle inhibitors and intermediates were studied using the same experimental model as above. The strategy is summarized in FIG. 2A, and the findings are shown in FIG. 2, B-D. First, the addition of 5 mM succinate to the arteriolar perfusate triggered a robust renin release (73±2Δ%), confirming the earlier data (11). The effects of succinate and high glucose levels did not appear to be additive (56±3Δ%; FIG. 2B). Then malonate, an inhibitor of the TCA cycle at the succinate dehydrogenase step (succinate degradation), was used. Malonate alone, in the presence of normal glucose (5.5 mM), caused significant renin release (54±7Δ%). Combining malonate with a high glucose level produced an augmented response (77±2Δ%). The effect of malonate was additive to that of succinate as well (83±4Δ%; FIG. 2B). Fluorocitrate was next used to block the TCA cycle enzyme aconitase, which is essential for producing succinate. The addition of fluorocitrate alone had no effect on renin release (11±2Δ%), but it abolished the effects of high glucose level on renin release (16±2Δ%). In subsequent studies, the dose-response relationship among succinate or malonate and renin release was established (FIG. 2C). The EC50 values for succinate and malonate were 335 and 367 μM, respectively. Administration of α-ketoglutarate (5 mM), another intermediate between the citrate and succinate steps, had no effect. Thus, Krebs-cycle intervention studies revealed that renin release specifically occurred in the presence of succinate. Using real-time imaging, the time course of high glucose level- and succinate-induced renin release was established (FIG. 2D). Succinate produced a more robust and rapid effect, consistent with the hypothesis that high glucose levels act through accumulating succinate levels. In addition to renin release, we observed substantial vasodilatation of the afferent arteriole within 3-4 minutes after treatment with high glucose levels.

Succinate Levels in Normal and Diabetic Kidney Tissue and Urine.

Figure 3:
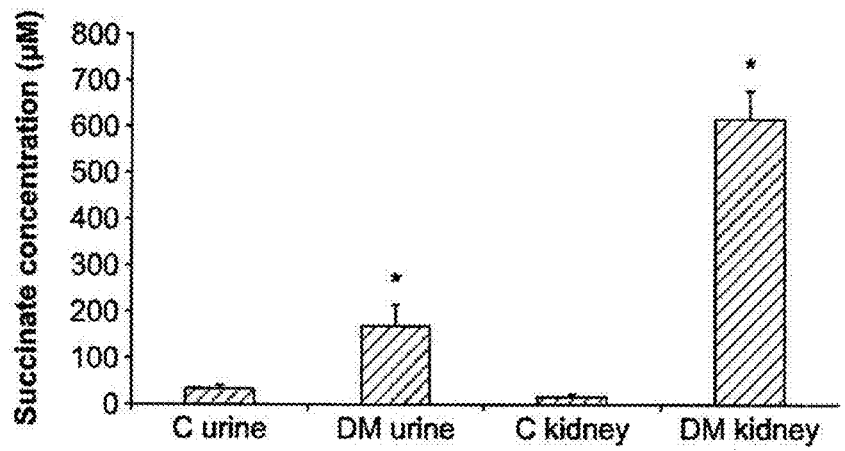
FIG. 3: Succinate accumulation in diabetic kidney tissue and urine. An enzyme assay and freshly harvested urine and whole kidney homogenates were used to estimate succinate accumulation in control (n=5) versus diabetic (DM; 1 week after STZ treatment; n=6) GPR91 WT mouse kidneys. Individual samples were measured in triplicates and averaged. *$P<0.001$ control vs. diabetic.

To demonstrate local accumulation of succinate in the diabetic kidney tissue to levels that are consistent with GPR91 activation, we measured succinate in nondiabetic and diabetic kidney tissue and urine (FIG. 3). In freshly harvested urine and whole kidney tissue samples of nondiabetic mice, the succinate concentration was 26±7.0 and 10±0.2 µM, respectively. In contrast, 1-2 orders of magnitude higher levels were detected in samples from diabetic mice 1 week after streptozotocin (STZ) injection (168±45 µM in urine; 616±62 µM in tissue).

GPR91 Specificity.

Figure 4:
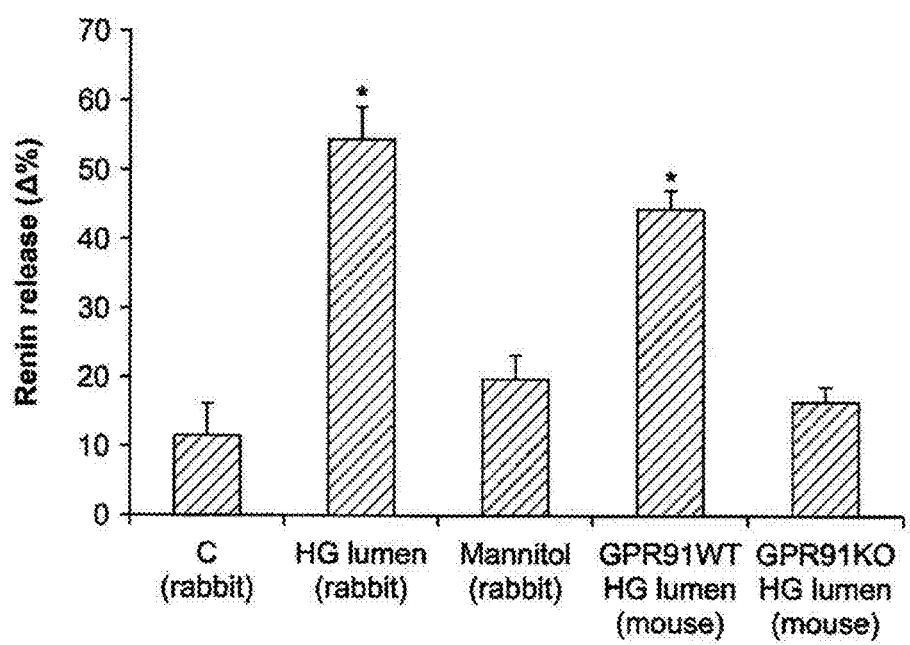
FIG. 4: High glucose level-induced renin release in GPR91+/+ and GPR91−/− mice. Effects of high glucose level (25.5 mM) on renin release, measured by the reduction in quinacrine fluorescence. Hyperosmotic control using mannitol is also shown (same data as in FIG. 1C). C, control baseline renin release. GPR91$^{+/+}$ (WT, n=6) and GPR91$^{−/−}$ (KO, n=4) mice were used. *$P<0.001$, control vs. high glucose lumen (rabbit, mouse).

Similar microperfusion experiments were performed using preparations dissected from GPR91+/+ and GPR91−/− mouse kidneys. Increasing glucose content of the afferent arteriole perfusate from 5.5 to 25.5 mM greatly stimulated the rate of renin release in GPR91+/+ mice, similar to that observed in rabbits (FIG. 1C). Granular content was reduced by 44±3Δ% within 30 minutes (FIG. 4). Importantly, high glucose level-induced renin release was diminished in GPR91−/− mice; granular content was reduced by only 16±3Δ%. Interestingly, the magnitude of this response is comparable to what was obtained before using mannitol for the control of osmolality effect (FIG. 1C). These data suggest that the effect of high glucose level on renin release has a minor hyperosmotic, but a very significant metabolic component. The succinate receptor GPR91 appears to be involved in the metabolic component, consistent with our main hypothesis that high glucose level triggers renin release through the accumulation of succinate and GPR91 signaling.

Localization of GPR91.

Figure 5:
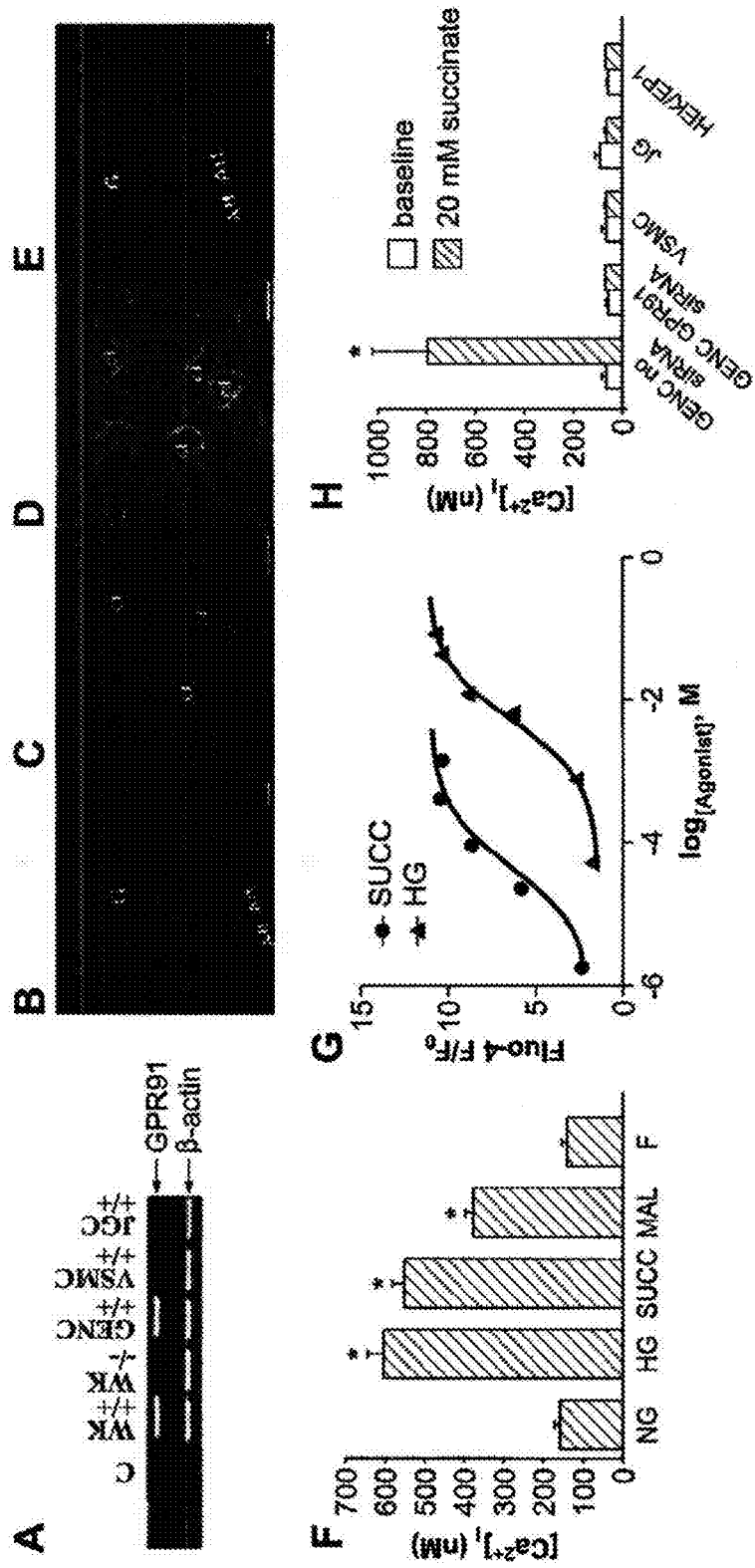
FIG. 5: Localization of GPR91 in GENCs. (A) Representative RT-PCR demonstrating the presence/absence of GPR91 in various mouse kidney cell types. C, control mix with no cDNA; WK, whole kidney from WT GPR91$^{+/+}$ or KO GPR91$^{−/−}$ mice. Same results were obtained in n=6 different samples each. JGC, renin-producing JG cells. (B-E) Localization of GPR91 protein in rat kidney with immunohistochemistry. (B) Strong GPR91 labeling (dark gray) was found in vascular endothelial cells, in both terminal afferent arteriole (Aff. art.) and glomerulus. One region of the glomerulus (indicated by a rectangle) is magnified in C and D for high-resolution colocalization studies. (C) Double labeling for rat endothelial cell marker RECA-1 (light gray) identified the endothelium of intraglomerular capillary loops (cl). (D) Overlay of GPR91 (dark gray) and RECA-1 (light gray) images shows colocalization (medium gray) of the 2 proteins in the same structures. DIC background is merged with fluorescence to show glomerular morphology. (E) Negative control using no GPR91 primary antibody. Nuclei are medium gray. Scale bar: 10 µm (B-E). (F) Elevations in GENC [$Ca^{2+}$]$_i$ levels from baseline (under normal glucose [NG], 5.5 mM) in response to high glucose level (25.5 mM) and TCA cycle inhibitors and intermediates. Succinate, 5 mM; malonate, 1 mM; fluorocitrate, 100 p.M. *$P<0.001$, compared with NG; n=9 each. (G) Dose-response relationship of high glucose level- and succinate induced elevations in GENC $Ca^{2+}$ levels; n=6 each. F/F$_0$, fluorescence (F) normalized to baseline (F$_0$). (H) Cell- and GPR91-specificity of the succinate induced [$Ca^{2+}$]$_i$ response. HEK cells were used for biosensor experiments (see below). *$P<0.001$, compared with baseline; n=6 each. Cells were grown on coverslips to near confluency, loaded with $Ca^{2+}$ sensitive fluorescent dye fura-2, and [$Ca^{2+}$]$_i$ was measured using a cuvette-based spectrofluorometer (Quantamaster-8; Photon Technology Inc.).

Molecular and functional studies were performed to identify the cell type(s) expressing GPR91 and involved in the generation of the renin release signal. RT-PCR was performed to detect GPR91 mRNA in mouse whole kidney and in cell cultures of various JGA cell types (FIG. 5A). Consistent with the role of the vascular endothelium in glucose-induced renin release (FIG. 1C), expression of the succinate receptor GPR91 was found on the mRNA level in a recently established glomerular endothelial cell (GENC) line (14). In contrast, primary cultures of VSMCs and JG cells produced no signal. Whole kidney tissue from GPR91+/+ and GPR91−/− mice served as positive and negative controls. To determine the localization of GPR91 protein in the kidney and in cells of the JGA in particular, immunohistochemistry on rat (FIG. 5, B-E), mouse, and rabbit kidney sections was performed using a recently produced, commercially available GPR91 polyclonal antibody. Vascular endothelial cells in the afferent arteriole and glomerulus, but not JG cells, were labeled positive for GPR91 (FIG. 5B). Endothelial localization was confirmed by double labeling with the rat endothelial marker RECA-1 (FIG. 5C). GPR91 and RECA-1 immunolabeling were localized to the same structures (FIG. 5D). This is consistent with the RT-PCR data above (FIG. 5A) and with our hypothesis that it is the vascular endothelium, rather than other JGA cells, that is capable of detecting extracellular succinate.

Additional functional studies tested whether GENCs that express GPR91, but not VSMCs and JG cells, produce elevations in cytosolic Ca2+ levels in response to the same TCA cycle inhibitors and intermediates that were used with in vitro renin release measurements (FIG. 2B). FIG. 5F shows significant elevations in GENC intracellular Ca2+ [Ca2+]i levels in response to high glucose level (605±36 nM), succinate (549±29 nM), and malonate (377±22 nM) compared with [Ca2+]i levels measured in presence of normal glucose (133±14 nM). Fluorocitrate failed to increase GENC [Ca2+]i levels (143±11 nM) (FIG. 5F). GENCs produced a substantial, dose-dependent Ca2+ signal when high levels of glucose or succinate were added to the superfusate, with an EC50 value of 11 mM and 69 µM, respectively (FIG. 5G). These data are consistent with the central role of succinate and the proposed Ca2+-coupled mechanism of GPR91 signaling (4). In addition, saturating doses of succinate did not cause [Ca2+]i elevations in VSMCs, JG cells, or HEK cells (FIG. 5H). Also, the succinate-induced response in GENCs was GPR91-specific, since silencing GPR91 with short, interfering RNAs (siRNA) produced no [Ca2+]i response (FIG. 5H).

Elements of the Paracrine Signal Transduction Cascade.

Figure 6:
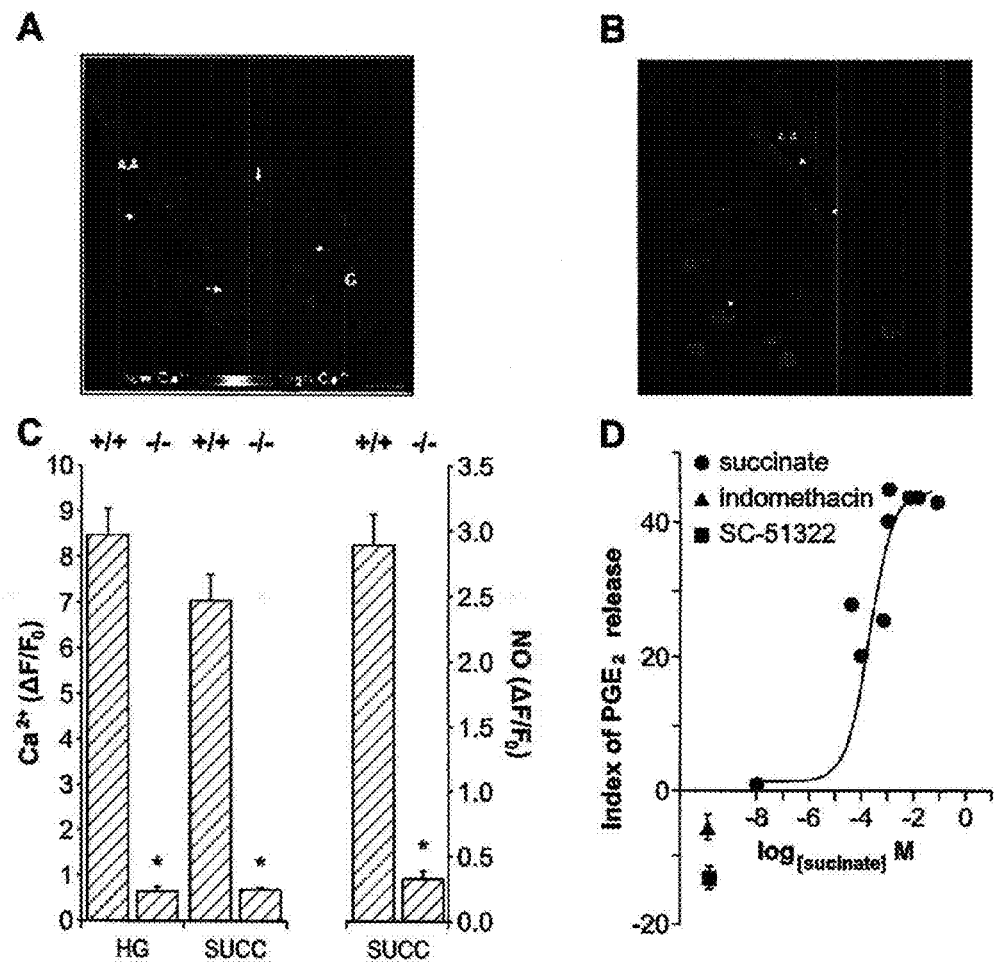
FIG. 6: GPR91 signaling in the vascular endothelium. Succinate- and GPR91-induced endothelial cytosolic $Ca^{2+}$ [$Ca^{2+}$]$_i$ signaling and NO production were studied using the microperfused mouse afferent arteriole-attached glomerulus preparation and confocal fluorescence microscopy with fluo-4/fura red ratiometric $Ca^{2+}$ (A) and DAF-FM imaging (B), respectively. Arrows point at glomerulus and afferent arteriole endothelial cells in situ. Scale bar: 20 µm. (C) Summary of the high glucose—(25.5 mM) and succinate—(5 mM) induced normalized changes in endothelial [$Ca^{2+}$]$_i$ and NO production in WT GPR91$^{+/+}$ or KO GPR91$^{−/−}$ kidney tissue. *$P<0.05$, WT ($^{+/+}$) vs. KO ($^{−/−}$); n=6 each. (D) Dose-response relationship of succinate-induced elevations in PGE$_2$ production and release from cultured GENCs, measured using a PGE$_2$ biosensor. Specially engineered biosensor cells, HEK293 cells, expressing the $Ca^{2+}$-coupled PGE$_2$ receptor EP1 were loaded with fluo-4 and positioned next to GENCs in culture. Effects of succinate on GENC PGE$_2$ production were measured based on the biosensor cell $Ca^{2+}$ signal, since upon PGE$_2$-binding these biosensor cells produce a $Ca^{2+}$ response detected by fluorescence imaging. The cyclooxygenase inhibitor indomethacin (50 μM) and EP1 receptor blocker SC-51322 (10 μM) in presence of 5-mM succinate both served as negative controls for $PGE_2$ specificity. Normalized changes in HEK293-EP1 biosensor cell fluo-4 intensity are shown and served as an index of $PGE_2$ release. n=6 for each dose.

Since endothelial cells are indispensable for high glucose level-induced renin release and are the only cell types in the terminal afferent arteriole to express GPR91, they appear to be key components of generating the renin release signal. Fluorescence imaging studies in the microperfused JGA measured endothelial intracellular Ca2+ ([Ca2+]i) changes and NO production (FIG. 6, A-C). Increasing glucose concentration from 5.5 to 25.5 mM or the addition of 5 mM succinate to the arteriolar perfusate caused significant elevations in [Ca2+]i and NO production in the vascular endothelium (FIG. 6C). In addition, the effect of high glucose level was GPR91-dependent (FIG. 6C). Since prostaglandins (PGE2 and PGI2) are classic mediators of renin release, further experiments tested if endothelial [Ca2+]i elevations trigger not only NO but also PGE2 production and release from GENCs (FIG. 6D). As expected, GENCs released PGE2 in response to succinate in a dose-dependent fashion with an EC50 value of 214 µM. These chemical mediators, NO and PGE2, are effective vasodilators and were most likely involved in the high glucose level-induced increase in afferent arteriole diameter observed simultaneously with renin release.

GPR91 Signaling in the STZ Model of Type 1 Diabetes In Vivo.

Figure 7:
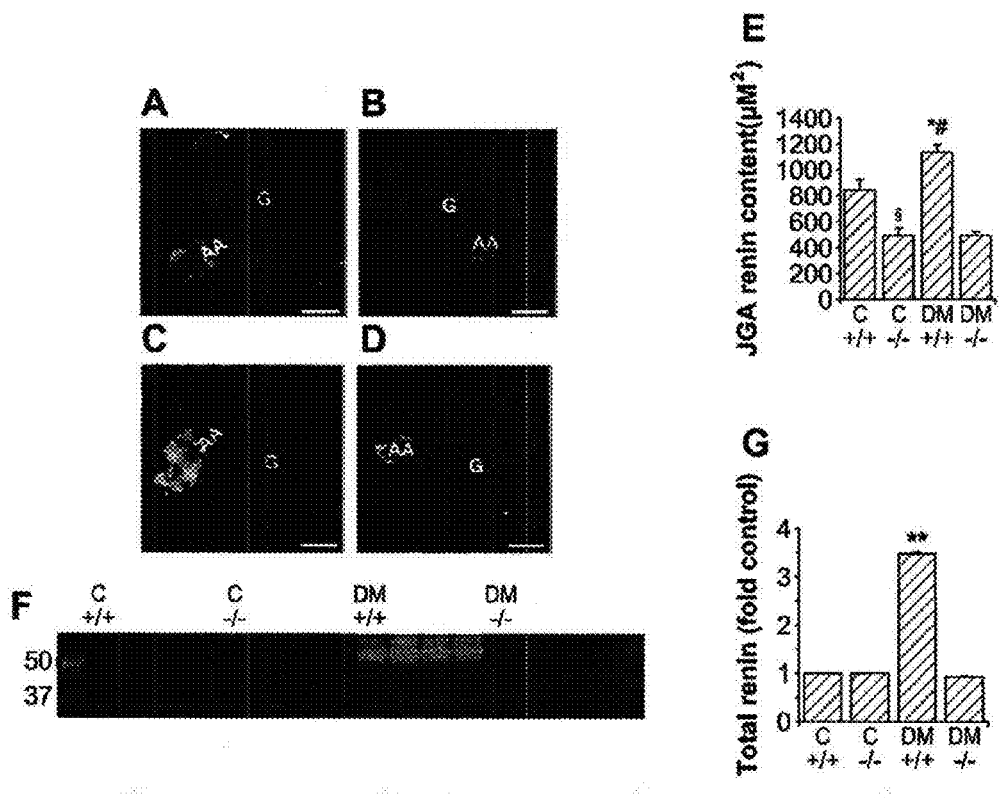
FIG. 7: Renin granular content in $GPR91^{+/+}$ and $GPR91^{-/-}$ mice in vivo. (A and B) Representative multiphoton fluorescence images of JGA renin content (light gray) in nondiabetic (A and B) and diabetic (C and D) $GPR91^{+/+}$ (A and C) and $GPR91^{-/-}$ (B and D) mouse kidneys. The intravascular space (plasma) was labeled using a 70-kDa dextran rhodamine conjugate (dark gray). Scale bar: 20 μm. (E) Summary of changes in JGA renin content in control and in the STZ model of type 1 diabetes (STZ-diabetic; DM) $GPR91^{+/+}$ and $GPR91^{-/-}$ mice. JGA renin content was calculated based on measuring the area of quinacrine fluorescence ($\mu m^2$).*P<0.05, C vs. DM $GPR91^{+/+}$; $^x$P<0.05, C $GPR91^{+/+}$ vs. C $GPR91^{-/-}$; #p<0.05, DM $GPR91^{+/+}$ vs. DM $GPR91^{-/-}$ (n=4 each). (F) Renin immunoblot (light gray) using control and STZ-diabetic $GPR91^{+/+}$ and $GPR91^{-/-}$ mouse whole kidney. Four samples are shown for each group. 8-actin (dark gray) served as loading control (G) Summary of changes in whole kidney renin content based on renin immunoblot densitometry. *P<0.05 C vs. DM $GPR91^{+/+}$; #p<0.05 DM $GPR91^{+/+}$ vs. DM $GPR91^{-/-}$ (n=4 each).

Whole animal studies were performed using GPR91+/+ and GPR91−/− mice to evaluate the in vivo importance of GPR91 in renin signaling in diabetic and nondiabetic control animals using the STZ model of type 1 diabetes (STZ-diabetes). A multiphoton imaging approach (15, 16) was used to directly visualize and quantity JGA renin granular content in the intact, living kidney (FIG. 7, A-E). Nondiabetic GPR91−/− mice had reduced JGA renin granular content compared with GPR91+/+ littermates (FIGS. 7, A, B, and E), although total renal renin content was not altered based on whole kidney immunoblotting (FIGS. 7, F and G). In GPR91+/+ mice, the STZ-diabetes caused a 3.5-fold increase in total renin (FIGS. 7, F and G) and a less pronounced but still significant increase in JGA renin granular content (FIG. 7, C-E). Importantly, both total and JGA renin were significantly reduced in GPR91−/− littermates with STZ-diabetes (FIGS. 7, E and G).

Discussion

The present work identified succinate as an important element of the diabetic milieu that links high level of glucose supply and metabolism with RAS activation. High glucose level, through the TCA cycle intermediate succinate and the activation of its receptor GPR91, acts directly and acutely on the JGA and triggers renin release, the rate-limiting step of RAS activation. The central role of RAS in the pathogenesis of diabetic nephropathy has been established in the past several decades; however, a unifying mechanism of RAS activation in both type 1 and type 2 diabetes has been sorely lacking (2). The presently identified GPR91-dependent paracrine JGA-signaling cascade provides, for what we believe to be the first time, a direct mechanism for the local intrarenal activation of RAS in diabetes.

Normally, succinate is present in mitochondria, but it is also found in the systemic circulation in the 1- to 20-μM range (17). However, succinate can accumulate extracellularly in peripheral tissues in certain pathophysiological states when energy and oxygen supply/demand are out of balance (5). Although, it is not feasible to measure succinate levels in the JGA interstitium, conditions of the renal cortical environment seem to be favorable for local succinate accumulation. In spite of high cortical blood flow, significant shunting of oxygen within the cortical, preglomerular vasculature between interlobular arteries and veins results in low cortical $pO_2$ values in the range of 40 mmHg (18). The nonlinear nature of single nephron blood flow (19) is another possible contributing factor. Hyperglycemia is associated with further, marked reductions in renal oxygen tension and mitochondrial respiration (20). Therefore (juxta)glomerular endothelial cells appear to be well suited and strategically positioned to sense the local accumulation of succinate. Consistent with this, we measured 1-2 orders of magnitude higher levels of succinate in the urine and kidney homogenates of diabetic animals 1 week after STZ injection compared with controls (FIG. 3). In addition, a recent report found similar but less pronounced changes in serum succinate levels in diabetes (21), further supporting the local, intrarenal accumulation of succinate. The present findings (FIGS. 5, F and G, and FIGS. 6, A and C) that GENCs, either in culture or in the native tissue, respond to high glucose level with dose-dependent, significant elevations in $[Ca2+]i$, a response which is GPR91 specific, further support local succinate accumulation. Although GENCs alone appear to be capable of generating extracellular succinate in amounts that trigger GPR91, other JGA cell types most likely contribute to the local succinate accumulation. GPR91 localization studies on both the mRNA and protein level (FIG. 5) identified the (juxta)glomerular endothelium as one possible sensor of local succinate. Succinate-induced GPR91 signaling in GENCs, either cultured (FIG. 5F) or freshly dissected (FIG. 6C), involved elevations in $[Ca2+]i$ and the production and release of NO and PGE2 (FIGS. 5 and 6), well established vasodilators and classic mediators of renin release from adjacent JG cells (8, 9). Although high, saturating concentrations of succinate (5 mM) were used in some studies, the low EC50 values resulting from the succinate effect on GENC $[Ca2+]i$ (69 μM), PGE2 production (214 μM), and renin release (335 μM) suggest that near physiological succinate levels can activate GPR91. The relatively higher EC50 values established with the PGE2 biosensor assay and the in vitro renin release model are not unexpected, since these are more downstream, complex, and highly regulated mechanisms; therefore, they are somewhat less sensitive. The involvement of NO and prostaglandins in high glucose level-induced (succinate-induced) renin release was also supported by in vitro microperfusion data (FIG. 1C), using blockers of the synthetic enzymes NOS and cyclooxygenase (COX). Nonselective inhibitors were used, since many isoforms of NOS (NOSI-III) (22, 23) and COX (COX-1 and -2) (24, 25) are present in the JGA. Importantly, NOSIII (endothelial NOS) and COX-2 are upregulated in diabetes (23, 25). Localization of GPR91 in the proximal and distal nephron (4) suggests other potential sites of succinate detection in the kidney and warrants further studies. It should be noted that numerous, well established, and ubiquitous dicarboxylate carriers and organic anion transporters are expressed in high amounts in the kidney, both in mitochondrial and cell membranes that transport succinate along its concentration gradient and that may be involved in extracellular succinate accumulation (26-28).

Inhibition of the Krebs cycle before or after the succinate step caused marked but differing changes in renin release (FIG. 2, A-C). At normal glucose levels, malonate, an inhibitor of the succinate dehydrogenase complex (29), caused robust renin release, the effect of which was markedly enhanced in the presence of high glucose level or succinate. In contrast, fluorocitrate, an inhibitor of aconitase (30, 31) and succinate production, blocked renin release induced by high glucose level. Consistent with these data and Ca2+-mediated GPR91 signaling, differing GENC Ca2+ level changes were observed with malonate and fluorocitrate (FIG. 5F). The opposite effects of these metabolic inhibitors suggest the specific role of succinate and exclude the possibility of tissue injury. Oxygen consumption and ATP production in the kidney remain constant after malonate and fluorocitrate administration in vivo (29, 31) due to the use of alternative substrates (glutamine). Also, the partial renin-releasing effect of osmolytes (controlled with mannitol) is consistent with a recent report (32) that acute increases in osmolality trigger renin release.

Figure 8:
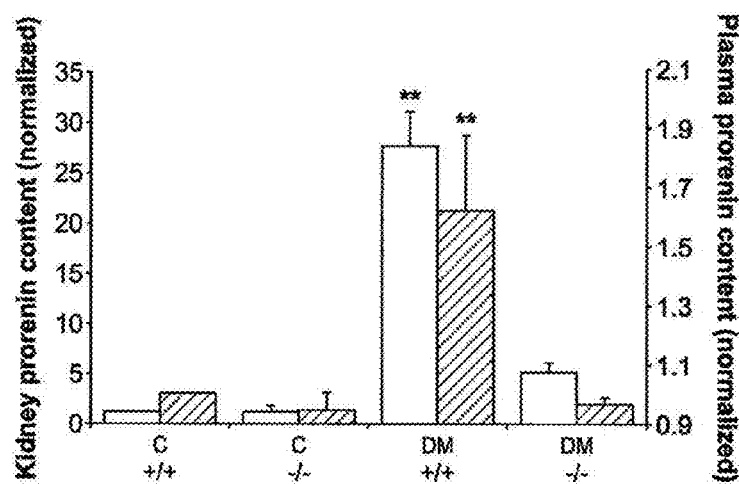
FIG. 8: Changes in whole kidney and serum prorenin content in control and STZ-diabetic GPR91+/+ and GPR91−/− mice. Prorenin was measured in whole kidney homogenates and serum as the difference between renin activity before and after trypsin activation of prorenin measured with a fluorescence renin enzyme essay. Compared to age-matched non-diabetic control animals, prorenin content of both whole kidney tissue and plasma samples increased significantly in diabetic animals. Diabetic $GPR91^{-/-}$ animals showed no change in kidney or serum prorenin content. *P<0.05, C vs. DM $GPR91^{+/+}$; #P<0.05, DM $GPR91^{+/+}$ vs. DM $GPR91^{-/-}$ (n=4 each).
Figure 9:
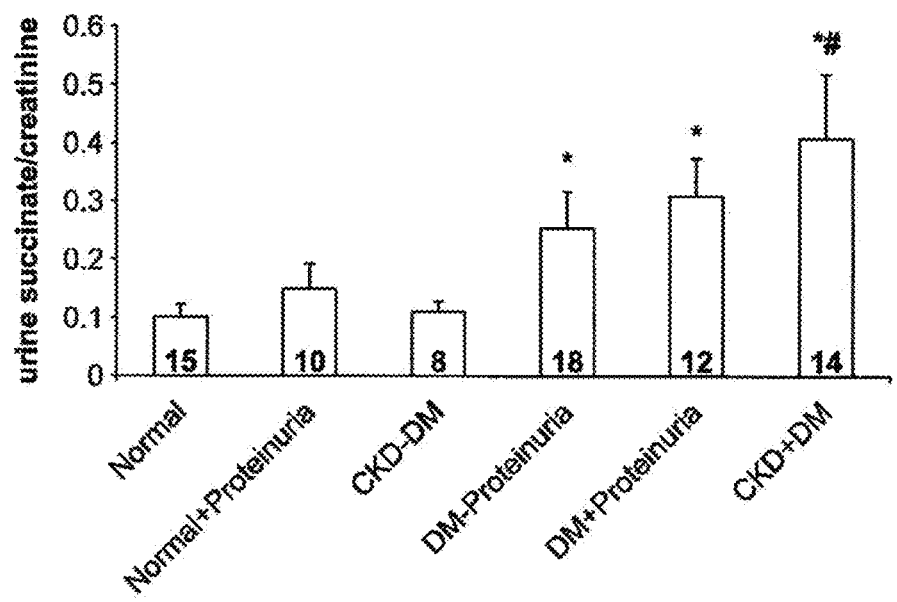
FIG. 9. Succinate content of human urine samples of different disease background. Spot urine samples were collected in 90 patients according to an IRB-approved protocol. The succinate/creatinine ratio was calculated because this gives a relative succinate content which is independent of variations in urinary concentration/dilution. Data represent mean±SEM, the number of patients in each group are shown in the columns. CKD: chronic kidney disease; DM: diabetes mellitus; P: proteinuria. *normal vs. DM−P, DM+P, CKD+DM, #CKD−DM vs. CKD+DM; P<0.05.

Reduced JGA renin content in control, nondiabetic GPR91−/− mice (FIGS. 7, B and E) suggests that succinate signaling through GPR91 is a physiological mechanism to control RAS activity, in addition to its potential role in diabetic pathology. Since the present in vivo studies focused on the early phase of diabetes, it will be interesting to study in future work the chronic phase of the disease and the role of GPR91 in the development of in vivo diabetic renal complications, such as proteinuria and hypertension. It should be noted, however, that further studies on the role of GPR91 in blood pressure control in diabetes are hampered by the lack of good mouse models of diabetic nephropathy (2, 33). Mice are resistant to a number of renal and systemic complications of diabetes, such as the lack of diabetes-induced hypertension (2, 33). Nevertheless, hypertension and systemic RAS activation may not be as central to diabetes as previously thought (1, 2), since the identification of the prorenin receptor in the kidney (34) and its local signaling provides an Ang II-independent alternative in the pathogenesis of diabetic renal damage (35, 36). The possible involvement of prorenin in GPR91-mediated renin granule exocytosis in diabetes (FIG. 8) is intriguing and consistent with the importance of the prorenin receptor and requires further study. Nevertheless, the present studies established that the elevation in plasma and kidney tissue prorenin, at least one in vivo parameter that is classic in diabetes, is GPR91-dependent. In addition to triggering renin release, GPR91-mediated NO and PGE2 production in the JGA could be an important causative mechanism of vascular smooth muscle and mesangial relaxation (FIG. 1C and FIG. 2D), resulting in glomerular hyperfiltration, another hallmark of early diabetes (1-3).

In summary, we identified a paracrine signaling mechanism within the JGA initiated by high glucose levels (such as those characteristic of diabetes), which directly activates renin synthesis and release and causes vasodilatation of the afferent arteriole. This signaling mechanism involves the (juxta)glomerular endothelium, a sensor of accumulating succinate levels in hyperglycemia through what we believe to be a novel metabolic receptor GPR91, Ca2+-coupled generation and release of endothelial NO and prostaglandins (at least PGE2), and their actions on adjacent JG renin-producing cells. We believe GPR91 is a new potential therapeutic target to prevent renal complications of diabetes.

Many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Ritz E., Dikow R. Hypertension and antihypertensive treatment of diabetic nephropathy. Nat. Clin. Pract. Nephrol. 2006; 2:562-567.
2. Gurley S. B., Coffman T. M. The renin-angiotensin system and diabetic nephropathy. Semin. Nephrol. 2007; 27:144-152.
3. Thomson S. C., et al. Ornithine decarboxylase, kidney size, and the tubular hypothesis of glomerular hyperfiltration in experimental diabetes. J. Clin. Invest. 2001; 107:217-224.
4. He W., et al. Citric acid cycle intermediates as ligands for orphan G-protein-coupled receptors. Nature. 2004; 429: 188-193.
5. Hebert S. C. Physiology: Orphan detectors of metabolism. Nature. 2004; 429:143-145.
6. Wittenberger T., Schaller H. C., Hellebrand S. An expressed sequence tag (EST) data mining strategy succeeding in the discovery of new G-protein coupled receptors. J. Mol. Biol. 2001; 307:799-813.
7. Schnermann, J., and Briggs, J. 1985. Function of the juxtaglomerular apparatus: local control of glomerular hemodynamics. In The kidney: physiology and pathophysiology. D. W. Seldin and G. Giebisch, editors. Raven Press. New York, N.Y., USA. 669-697.
8. Skøtt O. Renin. Am. J. Physiol. Regul. Integr. Comp. Physiol. 2002; 282:R937-R939.
9. Francois H., Coffman T. M. Prostanoids and blood pressure: which way is up? J. Clin. Invest. 2004; 114:757-759.
10. Nguyen G. Increased cyclooxygenase-2, hyperfiltration, glomerulosclerosis, and diabetic nephropathy: put the blame on the (pro)renin receptor? Kidney Int. 2006; 70:618-620.
11. Baumbach L., Leyssac P. P., Skinner S. L. Studies on renin release from isolated superfused glomeruli: effects of temperature, urea, ouabain and ethacrynic acid. J. Physiol. 1976; 258:243-256.
12. Peti-Peterdi J., Fintha A., Fuson A. L., Tousson A., Chow R. H. Real-time imaging of renin release in vitro. Am. J. Physiol. Renal Physiol. 2004; 287:F329-F335.
13. Toma I., Kang J. J., Peti-Peterdi J. Imaging renin content and release in the living kidney. Nephron Physiol. 2006; 103:p 71-p 74.
14. Akis N., Madaio M. P. Isolation, culture, and characterization of endothelial cells from mouse glomeruli. Kidney Int. 2004; 65:2223-2227.
15. Kang J. J., Toma I., Sipos A., McCulloch F., Peti-Peterdi J. Quantitative imaging of basic functions in renal (patho) physiology. Am. J. Physiol. Renal Physiol. 2006; 291: F495-F502.
16. Kang J. J., Toma I., Sipos A., McCulloch F., Peti-Peterdi J. Imaging the renin-angiotensin system: an important target of anti-hypertensive therapy. Adv. Drug. Deliv. Rev. 2006; 58:824-833.
17. Kushnir M. M., Komaromy-Hiller G., Shushan B., Urry F. M., Roberts W. L. Analysis of dicarboxylic acids by tandem mass spectrometry. High-throughput quantitative measurement of methylmalonic acid in serum, plasma, and urine. Clin. Chem. 2001; 47:1993-2002.
18. Schurek H. J., Jost U., Baumgartl H., Bertram H., Heckmann U. Evidence for a preglomerular oxygen diffusion shunt in rat renal cortex. Am. J. Physiol. 1990; 259:F910-F915.
19. Yip K. P., Holstein-Rathlou N. H., Marsh D. J. Mechanisms of temporal variation in single-nephron blood flow in rats. Am. J. Physiol. 1993; 264:F427-F434.
20. Palm F. Intrarenal oxygen in diabetes and a possible link to diabetic nephropathy. Clin. Exp. Pharmacol. Physiol. 2006; 33:997-1001.
21. Sadagopan N., et al. Circulating succinate is elevated in rodent models of hypertension and metabolic disease. Am. J. Hypertens. 2007; 20:1209-1215.
22. Tojo A., et al. Immunocytochemical localization of distinct isoforms of nitric oxide synthase in the juxtaglomerular apparatus of normal rat kidney. J. Am. Soc. Nephrol. 1994; 4:1438-1447.
23. Khamaisi M., et al. Role of renal nitric oxide synthase in diabetic kidney disease during the chronic phase of diabetes. Nephron Physiol. 2006; 102:p 72-p 80.
24. Breyer M. D., Harris R. C. Cyclooxygenase 2 and the kidney. Curr. Opin. Nephrol. Hypertens. 2001; 10:89-98.
25. Cheng H. F., Harris R. C. Cyclooxygenases, the kidney, and hypertension. Hypertension. 2004; 43:525-530.
26. Fiermonte G., et al. Organization and sequence of the gene for the human mitochondrial dicarboxylate carrier: evolution of the carrier family. Biochem J. 1999; 344:953-960. doi: 10.1042/0264-6021:3440953.
27. Markovich D., Murer H. The SLC13 gene family of sodium sulphate/carboxylate cotransporters. Pflugers Arch. 2004; 447:594-602.
28. Sekine T., Miyazaki H., Endou H. Molecular physiology of renal organic anion transporters. Am. J. Physiol. Renal Physiol. 2006; 290:F251-F261.
29. Scaduto R. C., Jr., Schoolwerth A. C. Effect of bicarbonate on glutamine and glutamate metabolism by rat kidney cortex mitochondria. Am. J. Physiol. 1985; 249:F573-F581.
30. Bogusky R. T., Aoki T. T. Early events in the initiation of ammonia formation in kidney. J. Biol. Chem. 1983; 258: 2795-2801.
31. Fine A. The effects of fluorocitrate on renal glutamine, lactate, alanine, and oxygen metabolism in the dog. Can. J. Physiol. Pharmacol. 1989; 67:641-644.
32. Kurtz A., Schweda F. Osmolarity-induced renin secretion from kidneys: evidence for readily releasable renin pools. Am. J. Physiol. Renal. Physiol. 2006; 290:F797-F805.
33. Breyer M. D., et al. Mouse models of diabetic nephropathy. J. Am. Soc. Nephrol. 2005; 16:27-45.
34. Nguyen G., et al. Pivotal role of the renin/prorenin receptor in angiotensin II production and cellular responses to renin. J. Clin. Invest. 2002; 109:1417-1427.
35. Ichihara A., et al. Prorenin receptor blockade inhibits development of glomerulosclerosis in diabetic angiotensin II type 1a receptor-deficient mice. J. Am. Soc. Nephrol. 2006; 17:1950-1961.
36. Takahashi H. et al. 2007. Regression of nephropathy developed in diabetes by (pro)renin receptor blockade. J. Am. Soc. Nephrol. 18:2054-2061.10.1681/ ASN.2006080820
37. Peti-Peterdi J. Calcium wave of tubulogmerular feedback. Am. J. Physiol. Renal Physiol. 2006; 291:F473-F480.
38. Kovacs G., et al. Neuronal nitric oxide synthase: its role and regulation in macula densa cells. J. Am. Soc. Nephrol. 2003; 14:2475-2483.

39. Inscho E. W., Belott T. P., Mason M. J., Smith J. B., Navar L. G. Extracellular ATP increases cytosolic calcium in cultured rat renal arterial smooth muscle cells. Clin. Exp. Pharmacol. Physiol. 1996; 23:503-507.
40. Wagner C. A., et al. A rapid enzymatic method for the isolation of defined kidney tubule fragments from mouse. Pflugers Arch. 2003; 446:623-632.
41. Jensen B. L., Friis U. G., Skott O. In vitro studies on renin release. Methods Mol. Med. 2003; 86:341-350.
42. Peti-Peterdi J., et al. Luminal NaCl delivery regulates basolateral PGE2 release from macula densa cells. J. Clin. Invest. 2003; 112:76-82.
43. Suzuki F., et al. The dominant role of the pro-segment of prorenin in determining the rate of activation by acid or trypsin: studies with molecular chimeras. Biochem. Biophys. Res. Commun. 2000; 267:577-580.
44. Peti-Peterdi J., Bell P. D. Cytosolic [Ca2+] signaling pathway in macula densa cells. Am. J. Physiol. 1999; 277: F472-F476.
45. Dunn K. W., et al. Functional studies of the kidney of living animals using multicolor two-photon microscopy. Am. J. Physiol. Cell Physiol. 2002; 283:C905-C916.

What is claimed is:

1. A non-invasive method for early diagnosis of potential kidney damage due to renin-angiotensin system activation in a diabetic subject, comprising:
   obtaining, non-invasively, a test urine sample from said diabetic subject;
   pre-treating said test urine sample with perchloric acid followed by KOH to neutralize the sample;
   determining a succinate level in said test urine sample by an enzymatic assay that oxidizes a stoichiometric amount of NADH corresponding to the level of succinate in the urine sample;
   comparing the succinate level in said test urine sample with a succinate level in a control sample, wherein said control sample is either from healthy subjects or diabetic subjects without kidney damage; and
   determining a diagnosis, wherein a diagnosis of kidney damage due to renin-angiotensin system activation is determined if:
   (1) the control sample is from healthy subjects and the succinate level in said test urine sample is at least four-fold higher than the succinate level in the control sample, or
   (2) the control sample is from diabetic subjects without kidney damage and the succinate level in said test urine sample is at least two-fold higher than the succinate level in the control sample.

2. The method according to claim 1, wherein the control sample is from diabetic subjects without kidney damage, and a diagnosis of kidney damage due to renin-angiotensin system activation is determined when the succinate level in said test urine sample is at least two-fold higher than the succinate level in the control sample.

3. A method for early diagnosis of kidney damage due to renin-angiotensin system activation in a subject suffering from diabetes, comprising:
   obtaining a test urine sample from said subject;
   pre-treating the test urine sample with perchloric acid followed by KOH to neutralize the sample;
   determining a succinate level in said test urine sample by an enzymatic assay that oxidizes a stoichiometric amount of NADH corresponding to the succinate level;
   comparing the succinate level in said test urine sample with a succinate level in a corresponding healthy non-diabetic control sample; and
   determining a diagnosis, wherein a diagnosis of likely kidney damage due to renin-angiotensin activation in said subject is determined if the succinate level in said test urine sample is at least 10 times higher than the succinate level in the corresponding control sample.

4. The method according to claim 3, wherein said corresponding control sample is urine from healthy subjects.

5. A non-invasive method for early detection of kidney damage due to renin-angiotensin system activation in a diabetic subject, comprising:
   obtaining a test urine sample from said diabetic subject;
   pre-treating said test urine sample with perchloric acid followed by KOH to neutralize the acid treated sample;
   determining a succinate/creatinine ratio in said test urine sample, wherein said determining step comprising performing an enzymatic assay that oxidizes a stoichiometric amount of NADH corresponding to the succinate level in the test urine sample;
   comparing said succinate/creatinine ratio in said test urine sample with a succinate/creatinine ratio in a control sample, wherein said control sample is from a healthy subject or a diabetic subject without kidney damage; and
   making a detection determination, wherein a detection of kidney damage due to renin-angiotensin system activation is determined if:
   (1) the succinate/creatinine ratio in said test urine sample is at least four-fold higher than in the control sample from healthy subjects, or
   (2) the succinate/creatinine ratio in said test urine sample is at least two-fold higher than in the control sample from diabetic subjects without kidney damage.

6. A method for early detection of kidney disease due to renin-angiotensin system activation in a diabetic subject comprising:
   obtaining a test urine sample from said diabetic subject;
   pre-treating said test urine sample with perchloric acid followed by KOH to neutralize the sample;
   determining a succinate/creatinine ratio in said test urine sample, said determining step comprising performing an enzymatic assay that oxidizes NADH in a stoichiometric amount corresponding to the succinate level in the test urine sample;
   comparing the succinate/creatinine ratio in the test urine sample with a succinate/creatinine ratio in a control sample, wherein said control sample is from a healthy subject; and
   making a detection determination, wherein detection of kidney disease in the diabetic subject is determined if said succinate/creatinine ratio in the test urine sample is at least four-fold higher than the succinate/creatinine ratio in the control sample.

7. The method according to claim 5, wherein said control sample is urine from diabetic subjects without kidney damage.

* * * * *

```
                        SEQUENCE LISTING

<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
gcagcgcatc gccttctatc                                                  20

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
gctgccttct gattcatgtg g                                                21

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
gtcgtctggg ccttagtgac c                                                21

<210> SEQ ID NO 4
<211> LENGTH: 22
<212> TYPE: DNA
<213> ORGANISM: Artificial
<220> FEATURE:
<223> OTHER INFORMATION: Synthetic

<400> SEQUENCE: 4
tgtgagaatt ggttggcaac ag                                               22

<210> SEQ ID NO 5
<211> LENGTH: 22
<212> TYPE: DNA
<213> ORGANISM: Artificial
<220> FEATURE:
<223> OTHER INFORMATION: Synthetic

<400> SEQUENCE: 5
tcggtccatg ctaatgacag tg                                               22
```